_United States Patent_ [19]

Beitner

[11] Patent Number: 4,654,323
[45] Date of Patent: Mar. 31, 1987

[54] METHOD AND COMPOSITION FOR THE THERAPEUTIC AND PROPHYLACTIC TREATMENT OF TRAUMA TO THE SKIN

[75] Inventor: Rivka Beitner, Raanana, Israel

[73] Assignee: Bar Ilan University, Ramat Gan, Israel

[21] Appl. No.: 762,807

[22] Filed: Aug. 2, 1985

Related U.S. Application Data

[63] Continuation of Ser. No. 670,482, Nov. 13, 1984, abandoned, which is a continuation-in-part of Ser. No. 619,274, Jun. 11, 1984, abandoned.

[51] Int. Cl.$^4$ .................. A61K 37/00; A61K 31/54
[52] U.S. Cl. .......................................... 514/9; 514/39; 514/157; 514/213; 514/221; 514/223; 514/224; 514/263; 514/323; 514/327; 514/602; 514/648
[58] Field of Search ................................ 514/9, 223

[56] References Cited

U.S. PATENT DOCUMENTS 4,443,446  4/1984  Cormier ............................. 424/247

OTHER PUBLICATIONS

Physicians Desk Reference (PDR) 26th ed., pp. 1292–1293 (1972).
Bibi, et al.–Acquired Local Resistance to Burns, Burns, 9, 387–393 (1983).
Chih-Chun et al.–Treatment of Burns, Shanghai Scientific & Technical Pub. (1982), pp. 31–38 & 263–265.
Hidada et al., Biopharmacological Assessment of Calmodulin Function; Utility of Calmodulin Antagonists, Reproduced in Calmodulin and Intracellular Ca++ Receptors, Kakuichi et al., 1983.
Levin et al., Molecular Pharmacology, 12, 581–589 (1976).

_Primary Examiner_—Leonard Schenkman
_Attorney, Agent, or Firm_—Hedman, Gibson Costigan & Hoare

[57] ABSTRACT

A novel method and composition are disclosed for the therapeutic and prophylatic treatment of trauma to the skin. In particular, burns, sunburn and frostbite are treated with compounds that have the ability to interfere with the action of calcium calmodulin complex. A preferred compound is trifluoperazine.

37 Claims, 1 Drawing Figure

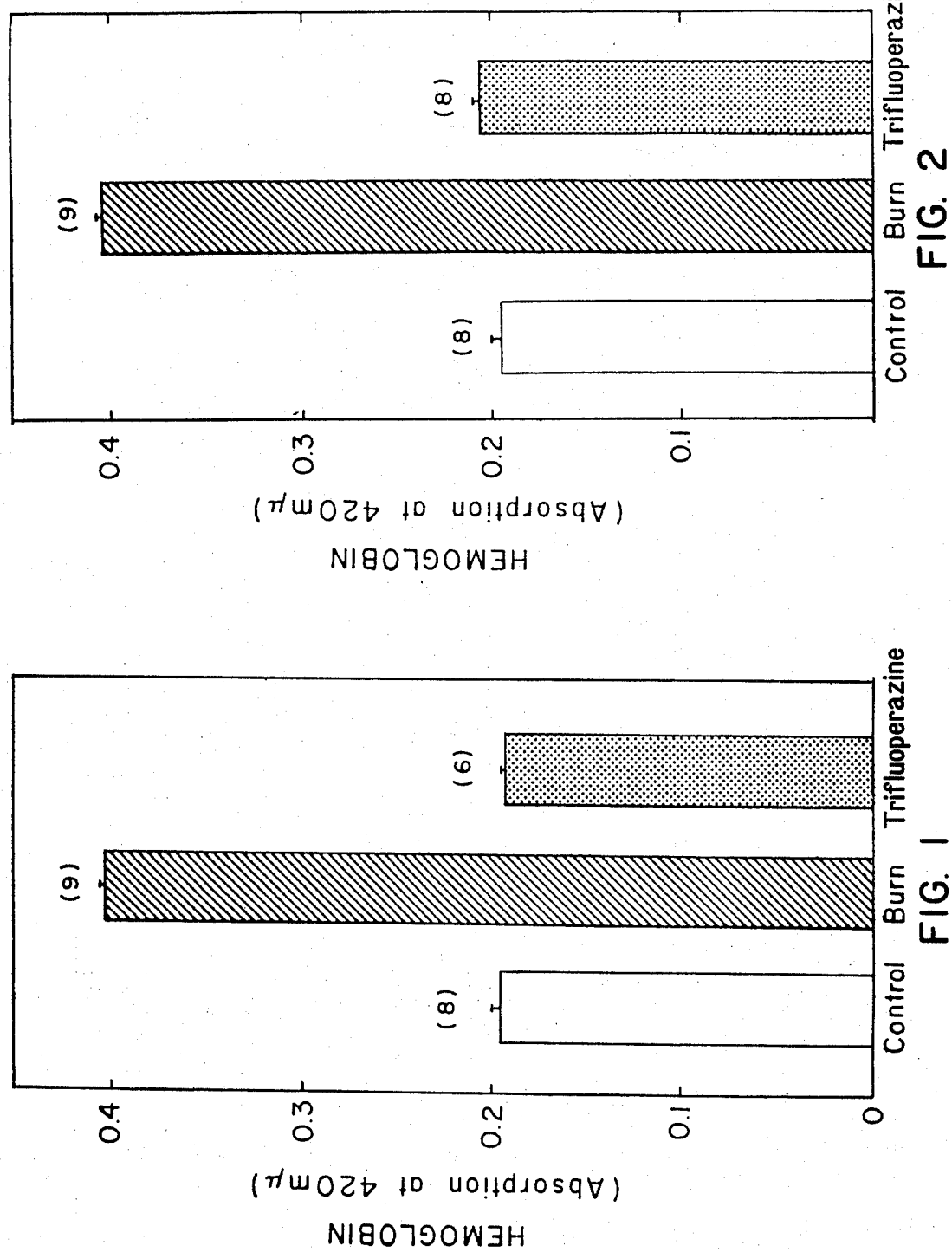

METHOD AND COMPOSITION FOR THE THERAPEUTIC AND PROPHYLACTIC TREATMENT OF TRAUMA TO THE SKIN

This application is a continuation of Ser. No. 670,482, filed Nov. 13, 1984 which is a continuation in part of Ser. No. 619,274 filed June 11, 1984 both now abandoned.

BACKGROUND OF THE INVENTION

In the prior art there is no known therapeutic agent that has been specifically used in the treatment of trauma to the skin, for example burns, sunburn and frostbite. The general prior art approach to skin trauma therapy has been limited to symptomatic treatment and the use of specific medicaments for the alleviation of pain, infection and electrolyte imbalances. Various types of bandages have been used as protective layers for the affected areas of the body and these have contained different anesthetic and anti-infective agents.

The applicant has discovered that a certain class of chemical substances is capable of exerting a profound effect on traumatized tissue, particularly burns, sunburn and frostbite. These compounds promote healing of skin tissue and aid in preventing or alleviating the damaging effects of trauma on the skin of the mammalian body. These chemical substances are characterized by an ability to interfere with the action of the calcium calmodulin complex in vivo in the mamaliam body. This effect has been observed when these chemical substances have been utilized topically or parenterally. Compounds that may be utilized for this purpose include those phenothiazines, thioxanthenes, butyrophenones, diphenylbutylamines, dibenzodiazepines, benzodiazepines, dibenzazepines and naphthalenesulfonamides, which have the aforesaid activity to interfere with calcium calmodulin activity. Accordingly it is a primary object of this invention to provide a novel composition and methods for treating trauma to the skin.

It is also an object of this invention to provide novel compositions and methods for preventing or alleviating the damaging effects of thermal and radiant energy produced by fire, steam, heated metal objects, hot fluids, thermonuclear explosions, exposure to sunlight, exposure to industrial ultra-violet sources and the like that cause burns and sunburn.

It is also an object of this invention to provide novel compositions and methods for preventing or alleviating the damaging effects of frostbite.

These and other objects of the invention will become apparent from a review of the detailed descriptions of the invention.

Compounds which are characterized by an ability to bind the protein calmodulin in vivo are known in the prior art. For example, U.S. Pat. No. 4,443,446 describes these compounds and their use as vaginal contraceptives. Many of these compounds have also been used for their antipsychotic action.

BRIEF DESCRIPTION OF THE DRAWINGS

FIGS. 1. and 2 are graphs that show the reduction of hemoglobin in the skin of an animal treated with a compound according to the invention.

DETAILED DESCRIPTION OF THE INVENTION

The invention provides novel compositions and methods for use in treating mammalian tissues that have been damaged by trauma induced by thermal, electrical, radiant, freezing or mechanical stresses. Also included are prophylatic methods of preventing or alleviating the damage to mammalian tissues that may be caused by subsequently induced trauma.

The methods of the invention may be practiced by the use of certain prior art parenteral compositions of compounds having the ability to interfere with action of the calcium calmodulin complex.

As used herein and in the appended claims, the term "compound having the ability to interfere with action of the calcium calmodulin complex" means all compounds that inhibit the in vivo actions of calcium-calmodulin complex sufficiently so that a trauma to mammalian skin will be prevented or alleviated. In particular the trauma may include a burn, sunburn or frostbite. These compounds include compounds known in the literature as anti-calmodulin compounds, calmodulin antagonists and calmodulin binding compounds. These various mechanisms that are involved are described in: Vincenzi, F.F., in Calmodulin and Intracellular $Ca++$ Receptors, (S. Kakiuchi et al editors), Plenum Press, NY (1982) pp 1–17, which is incorporated by reference.

Compounds which are known to have ability to interfere the action of calcium calmodulin complex include trifluoperazine, fluphenazine, thioridazine, chlorprothixene chlorpromazine, penfluridol, benperidol, haloperidol, pimozide, clozapine, medazepam, chlordiazepoxide, imipramine, amitriptyline, protriptyline, desipramine and naphthalenesulfonamides. In addition, this invention provides novel compositions for use in the practice of the invention. These compositions comprise: sterile and non-sterile topical ointments, creams or lotions which contain a compound having the ability to interfere with calcium calmodulin complex; sterile and non-sterile solutions for spray application from pressurized or non-pressurized containers which contain a compound having the ability to interfere with the action of calcium calmodulin complex with or without a local anesthetic; an electrolyte solution which also contains a compound having the ability to interfere with the action of calcium calmodulin complex; a bandage dressing which contains a compound having the ability to interfere with the action of calcium calmodulin complex; a composition which contains an anti-infective compound and said compound and a composition which contains an analgesic and said compound; disposable injectable syringes which contain a solution of a compound having the ability to interfere with the action of calcium calmodulin complex with or without an analgesic; collapsible tubes which contain a sterile or non-sterile ointment, cream or lotion based on a compound having the ability to interfere with the action of calcium calmodulin complex with or without an anti-infective agent and/or a local anesthetic agent; compositions for treatment of burns on the buccal mucosa or the esophogous which contain a thixotropic agent, a local anesthetic and a compound having the ability to interfere with the action of calcium calmodulin complex. Wax or stiff paste like compositions that are applied to the skin as frostbite preventatives or burn protective coatings. These compositions include lip coatings, nose coatings which contain a compound having the ability to interfere with the action of calcium calmodulin complex for application to the skin prior to exposure to low temperatures.

Compositions for the prevention of sunburn which include a sunscreen such as para-aminobenzioc acid may be combined with a compound having the ability to interfere with the action of calcium calmodulin complex to protect those who expect to be exposed to the harmful effects of the sun.

The topical ointment, cream or lotions may be based on any of the well known ointment bases, creams or lotions that are described in the literature or which are commerically available.

Suitable bases are described in Remingtons's Practice of Pharmacy 9th Edition, Cook et al., pp 286-296, Mack Pub Co. which is incorporated by reference. The concentration of the compound having the ability to interfere with the action of calcium calmodulin complex in the topical ointment cream or lotion may be any amount that is effective for treatment of burns, sunburn or frostbite or other trauma. These amounts are preferably between 1 and 50% or more preferably from 4% to 40% and most preferably 7.5 to 20% weight by total weight of composition. These compositions are preferably sterile so that they will not introduce any pathogenic organisms into a burn.

Solutions for spray applications may be for using any liquid vehicle that will provide a homogeneous dispersion of the active compounds. It is preferred to use a lipophillic vehicle that will adhere to the skin and facilitate percutaneous absorption of the active compounds. Suitable vehicles include fatty acids that are liquid at room temperature, liquid glycols, DMSO and the like. If necessary, pharmaceutically acceptable organic solvents may be utilized to dissolve or disperse the active compound. The compound may be preferred at from 1 to 50% preferably 4% to 50% and most preferably 7½ to 20% by weight. These solutions may be supplied in pressurized containers using any suitable inert gas as a propellant. The solution in the container should be sterile. A non-pressurized spray containers using conventional piston type applicators may also be utilized.

It is also contemplated that a suitable local anesthetic may be combined with the spray solution or with any topical preparation to provide immediate relief from the burn pain. These local anesthetics may be included at from 0.1 to 10% by weight of solutions depending on the particular local anesthetic. The useful local anesthetic include lidocaine hydrochloride, benzocaine and the like. Other local anesthetics are described in Text Books of Organic Medicinal and Pharmaceutical Chemistry. 3rd edition, Wilson et al., Lippincott Pub., 1956, pp 421-435, which is incorporated by reference.

Electrolyte solution containing conventional quantities of electrolyte may be combined with a compound having the ability to interfere with the action of calcium calmodulin complex. Examples of these solutions include Ringer's Lactate solution and Isotonic saline. These solutions may contain from 0.1 to 10 mg per liter of the active compounds. A bandage dressing may be made from a combination of an absorbent layer that is provided with a impervious backing material. The material is saturated with a solution containing from 1 to 50% preferably 4% to 40% and most preferably 7.5% to 20% by weight of the active compound. The back layer may be made from a Mylar film or an aluminum foil layer. The absorbent layer may be made from gauze or a woven cotton fabric. An additional layer may be used to prevent it from adhering to the skin.

Compositions may be made containing an anti-infective compound solution as a bacteriostatic, bacteriocidal, antibiotic or a fungicidal agent. The particular anti-infective compound should be used at a level that will prevent the growth of pathogenic organisms. These materials are well known and include quaternary ammonium salts, neomycin, bacitracin, polymyxin, amphotericin, silver sulfadiazine, mafenide acetate, cerium sulfadiazine, gentamicin or silver nitrate and the like. These materials may be used in conventional amounts such as are shown in the Physicans Desk Reference (PDR) 38th Edition which is incorporated by reference. The amount of the compounds having the ability to bind calmodulin will vary from 1 to 50%, preferably 4% to 40%; and most preferably 7.5% to 20% by weight.

Disposable syringes may be prefilled with solutions of the active compounds with or without an analgesic compound such as meperidene, morphine, pentazocine and alike. The amount of the analgesic may be within the conventionally used range as shown in the PDR. The amount of the active compounds may be within the range of the single dosage unit set forth herein.

Collapsible tubes fabricated from plastic or suitable metals may be prefilled with ointment, cream, lotion that contain active compounds in an amount by 1 to 50% preferably 4% to 40% and most preferably 7.5% to 20% by weight. In addition, these containers are preferably sterile and may also contain one of the anti-infective agents set forth above and a local anesthetic.

The active compounds may be added to conventional compositions used for skin rashes such as diaper rashes. These compositions include baby powder, baby lotion and ointments used for diaper rashes. In addition the active compounds may be used in the treatment of bed sores, skin ulcers and the healing of cuts, bruises and surgical incisions by selecting an appropriate composition.

The method of treating burns comprises the parenteral, oral or local administration of an amount of the active compound, that is effective to alleviate the symptoms of a burn. Generally, the parenteral dosage will vary depending on the host. The particular compound trifluoperazine has been utilized successfully in rats at levels of 80 mg/kg body weight administered as a single dose. Other dosage regimens may be used which comprise administering the compound in divided doses over a period of days depending on the severity of the burn, the size of the involved area and the host. Generally, for humans the parenteral dose may range from 1-25 mg or more given as a single dose or larger amounts may be given in divided doses. The mode of injection may be intravenous, subcutaneous, intramuscular or otherwise. The dose will depend on the particular compound chosen and may be adjusted to give the optimum response in a given subject. Administration may also be by means of slow intravenous drip with or without the adminstration of anti-infective agents or electrolytes usually given to severely burned patients. The compounds may also be administered orally using tablets, capsules, suspensions or aqueous solutions.

The compositions may be prepared using conventional techniques.

The particular compounds that may be used are selected using the procedure set forth by Levin et al. Mol. Pharmacol 12, 581-589 (1976) which is incorporated by reference. While Levin et al use the term "activator", it is now recognized that this material is the protein known as calmodulin. See Kakiuchi et al, supra pp 1–3. The criteria for the inclusion of a particular compound as one having the ability to interfere with the action of calcium calmodulin complex is that the compound prevent or alleviate a trauma to mammalian skin and that it have an $I_{50}$ (activated) value of less than 320 uM in the Levin, et al., supra phosphodiesterase inhibition test. Especially preferred are those compounds with an $I_{50}$ (activated) value of less than 100 uM. Many phenothiazines, thioxanthenes, butyrophenones, diphenylbutylamines, benzodiazepines, dibenzodiazepines, dibenzazepines and naphthalenesulfonamides that interfere with the action of calcium calmodulin complex are commercially available. A number of these compounds are described in Drills Pharmacology In Medicine, Di Palma, 4th Edition, pp 466–501 which is incorporated by reference and naphthelenesulfonamides are described in Hidaka, H. and Tanaka, T., Calmodulin and Intracellular $Ca^{++}$ receptors, (S. Kakuchi, et al, editors) Plenum Press, NY (1982) pp. 19–23, which is incorporated by reference. The presently preferred compound is trifluoperazine.

The applicant does not wish to be bound by any theory by which the invention operates but it is believed that the therapeutic action is based on the fact that in skin burns and other skin injuries, there is a rapid release of bradykinin and serotonin. Both of these hormones tend to increase the intracellular concentration of calcium ions which bind the protein calmodulin to form a calcium calmodulin complex. This complex activates phospholipase $A_2$. The activated phospholipase $A_2$ acts on the cell membrane phospholipids causing the destruction of the cell membrane. This causes the loss of proteins, enzymes and other cell components, and the loss of the integrity of the integumentary system as a barrier to invasion by pathogenic organisms. The calcium calmodulin complex also activates glucose 1,6-bisphosphatase which is the enzyme that degrades glucose -1, 6-bisphosphate which is involved with carbohydrate metabolism. The decrease in the concentration of glucose-1, 6-bisphosphate causes a decrease in glycolysis with the resulting decrease in adenosine tri-phosphate (ATP) concentration. The decrease in ATP concentration also contributes to the destruction of the cell membrane and the discharge of the cell contents as noted above. The calmodulin binding agents are believed to bind to the calciumcalmodulin complex and render it substantially biologically inert with regard to the activation of phospholipase $A_2$ and glucose-1, 6-bisphosphatase.

DESCRIPTION OF THE PREFERRED EMBODIMENTS

The following studies are illustrative of the invention and are not to be construed as a limitation on the scope of the invention.

The preferred compound, trifluoperazine, was utilized to heal burns, sunburns and frostbites. Burns were induced by pouring water at 100° C. on the skin of rats. The compound has a clearly visible effect on the skin in that it markedly reduced the redness of the skin after burning. Its effect was further investigated by measuring several biochemical parameters which characterize burns, sunburns and frostbites. The following parameters were measured:

(a) Hemoglobin: In the inflammatory response to thermal injury, increased capillary permeability is an early and important vascular event. Thermal injury causes the extravascular accumulation of erythrocytes (Green, K.L., Br. J. Exp. Pathol. 59: 38–47 (1978), and hemoglobin is released from the heat-altered red cells ("Leading Articles", Lancet 1: 153–155 (1960).

(b) ATP: A characteristic change of an injured tissue is a decrease in the concentration of ATP, namely, the cell energy.

(c) Enzyme's activities: In an injured tissue, due to the pathological changes in cell membrane, there is a loss from the cell of several enzymes. The activities of soluble 6-phosphogluconate dehydrogenase and particulate and soluble hexokinase were found to be markedly reduced in the burned skin.

(d) Protein: The concentration of protein in the burned skin is significantly decreased.

These experiments and their results will now be described in detail:

METHODS

Preparation and treatment of rat skins

Charles River albino rats, aged 8–10 days (15–22 g b.wt) fed ad libitum were used. Skin burns were induced in the rats under anesthesia by pouring water at 100° C. on the abdomen and chest area. Trifluoperazine was administered either prior to or after the induction of burns. Identical rats with and without burns served as controls. The skin from the abdomen and chest was removed and rapidly frozen between a pair of aluminium tongs precooled in liquid $N_2$. The subcutaneous fat was scraped off and discarded, and the frozen skins were stored in liquid $N_2$ until used (24 h.). The frozen skins were powdered in a mortar cooled liquid $N_2$ and the powder was used for extraction of ATP, hemoglobin, protein and enzymes.

Injection (a) Injection prior to inducing burns

The animals were injected intraperitoneally with trifluoperazine dihydrochloride (80 mg/kg body wt.) in 0.1 ml saline. One hundred minutes later skin burns were induced (at 100° C). After an additional 20 min., the skin was removed and the biochemical parameters were assayed.

(b) Injection after burning

The animals were injected immediately after burning with the same solution as in (a) and the effects were studied 1 hour later.

Cream 400 mg of trifluoperazine dihydrochloride was mixed with 5 g of "Oil of Olay Beauty Fluid" (Olay Company Inc.) and applied topically.

Extraction and determination of ATP

The frozen skin powder (70–90mg) was placed on top of 1 ml frozen 5% perchloric acid containing 1 mM EDTA, and extracted at −10° C. After centrifugation, the extract was neutralized with KOH. The precipitated potassium perchlorate was removed by centrifugation and the clear supernatant was used for determination of ATP. ATP was measured as described by Lowry et al. (Lowry, O. H., Passonneau, J. V., Hasselberger, F. X. and Schulz, D. W., J. Biol. Chem. 239: 18–30 (1964).

Preparation and assay for hemoglobin and enzymes

The mitochondrial and soluble fractions were separated, and hexokinase and 6-phosphogluconate dehydrogenase activities were assayed as described by Beitner et al. (Beitner, R., Lilling, G., Frucht, H., Ben-Porat, H., and Sofer, Y., Biochem. Med. 30: 369–380 (1983). 100 ul of the soluble fraction was added to 1 ml of 0.25 M sucrose and hemoglobin was estimated spectrophotometrically at 420 mu.

Protein determination

Protein was measured by the method of Lowry et al. (Lowry, O. H., Rosenbrough, N. J., Farr, A. L. and Randall, R. J., J. Biol. Chem. 193:265-275 (1951) with crystalline bovine serum albumin as a standard.

FIG. 1 is a diagram showing the reversal of the effect of burns on hemoglobin content in rat skin by injection of trifluoperazine.

The effect of burns on hemoglobin contents in rat skin with and without trifluoperazine was demonstrated by injection of trifluoperazine prior to and after the induction of burns. Hemoglobin was extracted and assayed as described above in Methods and the results are shown in the attached FIG. 1 in which part A shows the results where trifluoperazine was injected prior to the induction of burns and part B the results where the injection was after the induction of burns. Values are means±SE with the number of experiments in parentheses, P values (burns vs. control or trifluoperazine vs. burns) are smaller than 0.005.

The control in each case was unburnt and untreated skin. "Burn" means burnt and untreated skin and "Trif" means treatment with trifluoperazine as specified.

The reversal of the effect of burns on ATP concentration in rat skins by injection of trifluoperazine prior to the induction of burns (A) or after burning (B) was demonstrated and the results are shown in the following Table 1:

TABLE 1

| Conditions | ATP (μmoles/kg wet wt) | |
| --- | --- | --- |
| | A | B |
| Control | 1211 ± 43 (12) | 1211 ± 43 (12) |
| Burn | 391 ± 38 (11) | 415 ± 39 (12) |
| Trifluoperazine | 1071 ± 165 (6) | 937 ± 130 (6) |

ATP was extracted and assayed as described in Methods. Values are means±S.E., with number of experiments in parentheses. P values (burns vs. control or trifluoperazine vs. burn)<0.005.

The reversal of the effect of burns on the activity of soluble 6-phosphogluconate dehydrogenase in rat skin by injection of trifluoperazine prior to induction of burns (A) and after burning (B) was demonstrated and the results are shown in the following Table 2:

TABLE 2

| Conditions | 6-Phosphogluconate dehydrogenase activity (m unit/mg protein) | |
| --- | --- | --- |
| | A | B |
| Control | 13.86 ± 0.42 (16) | 13.86 ± 0.42 (16) |
| Burn | 7.04 ± 0.23 (11) | 6.96 ± 0.22 (13) |
| Trifluoperazine | 11.89 ± 0.55 (14) | 10.32 ± 0.34 (11) |

Enzyme was extracted and assayed as described in Methods. Values are means±S.E., with number of experiment in parentheses. P values (burn vs. control or trifluoperazine vs. burn)<0.005.

The reversal of the effect of burns on the activity of soluble and mitochondrial hexokinase in rat skin by injection or trifluoperazine prior to inducing burns (A) and after burning (B) was demonstrated and the results are shown in the following Table 3:

TABLE 3

| Conditions | Mitochondrial hexokinase activity (munit/mg protein) | | Soluble hexokinase activity (munit/mg protein) | |
| --- | --- | --- | --- | --- |
| | A | B | A | B |
| Control | 2.38 ± 0.19 (8) | 2.38 ± 0.19 (8) | 1.57 ± 0.07 (8) | 1.57 ± 0.07 (8) |
| Burn | 0.86 ± 0.05 (6) | 0.85 ± 0.04 (6) | 0.60 ± 0.05 (6) | 0.55 ± 0.04 (6) |
| Trifluoperazine | 1.52 ± 0.12 (6) | 1.40 ± 0.14 (6) | 1.02 ± 0.05 (6) | 0.99 ± 0.05 (6) |

Values are means±S.E., with number of experiments in parentheses. P values (burn vs. control or trifluoperazine vs. burn)—0.005.

The reversal of the effect of burns on protein concentration in rat skin by injection of trifluoperazine prior to the induction of burns (A) or after burning (B) was demonstrated and the results are shown in the following Table 4:

TABLE 4

| Conditions | Protein (g/kg wet wt) | |
| --- | --- | --- |
| | A | B |
| Control | 3.940 ± 0.304 (8) | 3.940 ± 0.304 (8) |
| Burn | 2.254 ± 0.100 (6) | 2.543 ± 0.172 (6) |
| Trifluoperazine | 3.419 ± 0.284 (6) | 3.952 ± 0.373 (6) |

Protein was measured in the soluble fraction, as described in Methods. Values are means±S.E., with number of experiments in parentheses. P values (burn vs. control or trifluoperazine vs. burn)<0.005.

The reversal of the effect of burns on hemoglobin content in rat skin by trifluoperazine adminstered topically in the form of a cream was demonstrated and the results are show in the following Table 5:

TABLE 5

| Conditions | Hemoglobin (Absorption at 420 mμ) |
| --- | --- |
| Control | 0.18 ± 0.02 (8) |
| Burn | 0.46 ± 0.03 (10) |
| Trifluoperazine | 0.25 ± 0.02 (10) |

Trifluoperazine was administered topically in the form of a cream, immediately following the induction of burns (at 100° C.), and reapplied 1 hr later (total of two applications). After an additional hr (i.e., 2 hr from onset of burns), the skin was removed and hemoglobin extracted and assayed, as described in Methods. Values are means±S.E., with number of experiments in parentheses. P values (burns vs. control or trifluoperazine vs. burn)<0.005.

Reversal of the effect of burns on ATP concentration in rat skin by trifluoperazine administered topically in the form of a cream was demonstrated and the results are shown in the following Table 6:

TABLE 6

| Conditions | ATP (μmoles/kg wet wt) |
|---|---|
| Control | 1308 ± 88 (5) |
| Burn | 368 ± 56 (5) |
| Trifluoperazine | 750 ± 650 (5) |

Trifluoperazine was administered topically, as described in Table 5. ATP was extracted and assayed, as described in Methods. Values are means±S.E., with number of experiments in parentheses. P Values (burn vs. control or trifluoperazine vs. burn)<0.005.

TABLE 6a

Reversal of the effect of burns on ATP concentration in rat skin by trifluoperazine administered topically in the form of a cream

| Conditions | ATP (μmoles/kg wet wt) |
|---|---|
| Control | 1052 ± 34 (6) |
| Burn | 382 ± 54 (6) |
| Trifluoperazine | 1033 ± 86 (6) |

Trifluoperazine was administered topically in the form of a cream, immediately following the induction of burns, and reapplied 30 minutes later, and then every hour (total of seven applications). After 5½ hours from onset of burns, the skin was removed from each animal and ATP extracted and assayed, as described in Methods. Values are means±S.E., with number of experiments in parentheses. P values (burn vs. control or trifluoperazine vs. burn)<0.005.

Reversal of the effect of burns on the activity of soluble 6-phosphogluconate dehydrogenase in rat skin by trifluoperazine administered topically in the form of a cream was demonstrated and the results are shown in the following Table 7:

TABLE 7

| Conditions | 6-phosphogluconate dehydrogenase activity (m unit/mg protein) |
|---|---|
| Control | 16.30 ± 0.59 (7) |
| Burn | 7.30 ± 0.24 (15) |
| Trifluoperazine | 12.49 ± 0.44 (11) |

Trifluoperazine was administered topically, as described in Table 5. Enzyme was extracted and assayed, as described in Methods. Values are means±S.E., with number of experiments in parentheses. P values (burns vs. control or trifluoperazine vs. burn)<0.005.

The reversal of the effect of burns on the activity of soluble and mitochondrial hexokinase in rat skin by trifluoperazine adminstered topically in the form of a cream was demonstrated and the results are shown in the following Table 8:

TABLE 8

| Conditions | Mitochondrial hexokinase Activity (m unit/mg protein) | Soluble hexokinase Activity (m unit/mg protein) |
|---|---|---|
| Control | 2.33 ± 0.23 (6) | 1.77 ± 0.18 (6) |
| Burn | 0.88 ± 0.05 (6) | 0.69 ± 0.02 (6) |
| Trifluoperazine | 1.73 ± 0.12 (7) | 1.15 ± 0.09 (7) |

Trifluoperazine was administered topically, as described in Table 5. Hexokinase was extracted and assayed, as described in Methods. Values are means±S.E., with number of experiments in parentheses. P values (burn vs. control or trifluoperazine vs. burn)<0.005.

Reversal of the effect of burns on protein concentration in rat skin by trifluoperazine administered topically in the form of a cream was demonstrated and the results are shown in the following Table 9:

TABLE 9

| Conditions | Protein (g/kg wet wt) |
|---|---|
| Control | 4.160 ± 0.177 (6) |
| Burn | 2.646 ± 0.067 (6) |
| Trifluoperazine | 3.517 ± 0.076 (7) |

Trifluoperazine was administered topically, as described in Table 5. Protein was measured in the soluble fraction, as described in Methods. Values are means±S.E., with number of experiments in parentheses. P values (burn vs. control or trifluoperazine vs. burn)<0.005.

RESULTS (a) Effects or trifluoperazine administered as an injectible solution

When trifluoperazine was injected 100 min prior to inducing burns, it completely prevented the increase in hemoglobin content, and its concentration was similar to that of normal control skins. Similar results were obtained when trifluoperazine was injected immediately after burning and its effect was studied 1 hr later. Treatment with trifluoperazine completely reversed the effect of burning on hemoglobin content.

The experiments demonstrated in Table 1 show the effect of trifluoperazine on ATP concentration in skin. It can be seen that burning induced a marked decrease in the levels of ATP in skin, whereas injection of trifluoperazine 100 min prior to inducing burns (A) almost completely prevented the decrease in the concentration of ATP. Similar results were obtained when trifluoperazine was injected after burning and its effects studies 1 hour later (B).

As shown in Table 2, under identical conditions, trifluoperazine also antagonized the effect of burns on the activity of soluble 6-phosphogluconate dehydrogenase. The activity of this enzyme, which is markedly reduced by burns, was almost completely restored by injection of trifluoperazine either prior to inducing burns (A) or after burning (B). Similar results were obtained for hexokinase (Table 3). Burns induced a marked decrease in the activity of this enzyme from both the mitochondrial and soluble fractions and trifluoperazine antagonized this effect when injected either prior to inducing burns (A) or after burning (B).

The results presented in Table 4 show the effect of trifluoperazine on protein concentration in the soluble fraction from rat skin. It can be seen that burning induced a significant decrease in protein concentration, whereas injection of trifluoperazine prior to inducing burns (A), or after burning (B), reversed this effect.

(b) Effects of trifluoperazine administered topically in the form of a cream

The results presented in Tables 5-9 show the effects of trifluoperazine administered topically to the burned skin in the form of a cream. It can be seen that the effects of trifluoperazine applied in the form of a cream for 2 hours from onset of burns were similar to those obtained by the injectale solution. Namely, the cream reversed the changes in hemoglobin, ATP and protein concentration induced by burns (Tables 5, 6 and 9 respectively).

It is also reversed the reduction in enzymes' activities in the burned skin (Tables 7 and 8).

These results show that trifluoperazine is very effective in the treatment and prevention of burns. It prevented and abolished the marked changes in the skin content of hemoglobin, ATP, protein and enzymes' activities induced by burns. It also has a clearly visible effect on the skin.

Similar results are obtained in the treatment of sunburn and frostbite.

Since the compound acts both by treating and preventing burns, sunburns and frostbite, it may be used both in first aid and burn treatment and also to protect persons exposed to fire or the sun in the course of their daily work (e.g. soldiers, firemen, outdoor workers, etc.) and as protective measure in those plants and factories where employees work with fire.

It has been found that trifluoperazine is effective in the treatment of frostbite injuries. Frostbite was induced in rats under anesthesia by applying dry ice to the skin in the abdomen area. Trifluoperazine was administered topically to the frost-injured skin in the form of 20% by weight dispersion in "Oil of Olay Beauty Fluid" (Olay Company Inc). The results as reported in Tables 10-13 show the effects on hemoglobin, ATP, and enzymes' activities in the frost injured skin. It can be seen that the changes in these biochemical parameters induced by frostbite are similar to those induced by burns, namely, and increase in hemoglobin concentration and a decrease in ATP, and enzymes' activities. These experiments reveal that trifluoperazine reverses the changes in all these biochemical parameters to normal control levels.

TABLE 10

Effect of frostbite on hemoglobin content in rat skin and its reversal by trifluoperazine administered topically in the form of a cream

| Conditions | Hemoglobin (Absorption at 420 mμ) |
|---|---|
| Control | 0.14 ± 0.001 (7) |
| Frostbite | 0.32 ± 0.030 (11) |
| Trifluoperazine | 0.16 ± 0.001 (20) |

Frostbite was induced in the rats under anesthesia by applying dry ice for 1 minute to the skin in the abdomen area. Trifluoperazine was administered topically in the form of a cream, immediately following the induction of frostbite, and reapplied 30 minutes later, and then every hour. After 5½ hours from the induction of frostbite, a section of the affected skin was surgically removed and hemoglobin extracted and assayed, as described supra. Values are means±S.E., with number of experiments in parentheses. P values (frostbite vs. control or trifluoperazine vs. frostbite) <0.005.

TABLE 11

Effect of frostbite on ATP concentration in rat skin and its reversal by trifluoperazine administered topically in the form of a cream

| Conditions | ATP (μmoles/kg wet wt) |
|---|---|
| Control | 1087 ± 63 (8) |

TABLE 11-continued

Effect of frostbite on ATP concentration in rat skin and its reversal by trifluoperazine administered topically in the form of a cream

| Conditions | ATP (μmoles/kg wet wt) |
|---|---|
| Frostbite | 348 ± 48 (8) |
| Trifluoperazine | 979 ± 59 (14) |

Trifluoperazine was administered topically, as described in Table 10. ATP was extracted and assayed, as described in Methods. Values are means±S.E., with number of experiments in parentheses. P values (frosbite vs. control or trifluoperazine vs.frostbite) <0.005.

TABLE 12

Effect of frostbite on the activity of soluble 6-phosphogluconate dehydrogenase in rat skin and its reversal by trifluoperazine administered topically in the form of a cream

| Conditions | 6-phosphogluconate dehydrogenase activity (m unit/mg protein) |
|---|---|
| Control | 17.73 ± 0.59 (6) |
| Frostbite | 5.67 ± 0.24 (6) |
| Trifluoperazine | 15.45 ± 0.41 (6) |

Trifluoperazine was administered topically, as described in Table 10. Enzyme was extracted an assayed, as described in Methods. Values are means±S.E., with number of experiments in parentheses. P value (frostbite vs. control or trifluoperazine vs. frostbite) <0.005.

TABLE 13

Effect of frostbite on the activity of soluble and mitochondrial hexokinase in rat skin and its reversal by trifluoperazine administered topically in the form of a cream

| Conditions | Mitochondrial hexokinase activity (m unit/mg protein) | Soluble hexokinase activity (m unit/mg protein) |
|---|---|---|
| Control | 2.93 ± 0.11 (6) | 2.09 ± 0.07 (6) |
| Frostbite | 1.65 ± 0.07 (6) | 1.00 ± 0.05 (6) |
| Trifluoperazine | 3.22 ± 0.17 (6) | 1.99 ± 0.08 (6) |

Trifluoperazine was administered topically, as described in Table 10. Hexokinase was extracted and assayed, as described in Methods. Values are means±S.E., with number of experiments in parentheses. P values (frostbites vs. control or trifluoperazine vs. frostbite) <0.005.

Trifluoperazine was also found to be effective in the prevention and treatment of sunburn. Sunburn was induced in rats under anesthesia by exposing their skin in the abdomen area to a UV lamp (Osram-Sonnenstrahler Ultra-Vitalux ®), which closely resembles natural sunlight. The distance between lamp and the animal was 17.5 cm and the time of exposure was 1½-2 minutes. Trifluoperazine was administered either as an injectable solution (2 mg per rat) or topically in the form of a cream (8% of trifluoperazine in Oil of Olay.)

Tables 14-21 show the effects of trifluoperazine on hemoglobin, ATP, and enzymes activity in the sunburned skin. It can be seen that trifluoperazine administered either as an injectable solution or topically in the form of a cream, reversed the changes in these biochemical parameters.

These results show that trifluoperazine has utility in the treatment of sunburn.

TABLE 14
Effect of sunburn on hemoglobin content in rat skin and its reversal by trifluoperazine administered as in injectable solution

| Conditions | Hemoglobin (absorption at 420 mµ) |
|---|---|
| Control | 0.16 ± 0.015 (18) |
| Sunburn | 0.56 ± 0.025 (15) |
| Trifluoperazine | 0.15 ± 0.010 (14) |

Values are means±S.E., with number of experiments in parentheses. P values (sunburn vs. control or trifluoperazine vs. sunburn)<0.005.

TABLE 15
Effect of sunburn on ATP concentration in rat skin and its reversal by trifluoperazine administered as an injectable solution

| Conditions | ATP (µmoles/kg wet wt.) |
|---|---|
| Control | 1136 ± 65 (10) |
| Sunburn | 393 ± 30 (9) |
| Trifluoperazine | 922 ± 52 (12) |

Values are means±S.E., with number of experiments in parentheses. P values (sunburn vs. control or trifluoperazine vs. sunburn)<0.005.

TABLE 16
Effect of sunburn on the activity of soluble 6-phosphogluconate dehydrogenase in rat skin and its reversal by trifluoperazine administered as an injectable solution

| Conditions | 6-phosphogluconate dehydrogenase activity (m unit/mg protein) |
|---|---|
| Control | 21.26 ± 0.47 (10) |
| Sunburn | 14.33 ± 0.47 (18) |
| Trifluoperazine | 21.13 ± 0.54 (15) |

Values are means±S.E., with number of experiments in parentheses. P values (sunburn vs. control or trifluoperazine vs. sunburn)<0.005.

TABLE 17
Effect of sunburn on the activity of soluble and mitochondrial hexokinase in rat skin and its reversal by trifluoperazine administered as an injectable solution.

| Conditions | Mitochondrial hexokinase Activity (m unit/mg protein) | Soluble hexokinase Activity (m unit/mg protein) |
|---|---|---|
| Control | 3.40 ± 0.17 (9) | 2.33 ± 0.09 (9) |
| Sunburn | 1.13 ± 0.08 (9) | 1.29 ± 0.07 (9) |
| Trifluoperazine | 2.54 ± 0.19 (9) | 2.07 ± 0.11 (9) |

Values are means±S.E., with number of experiments in parentheses. P values (sunburn vs. control or trifluoperazine vs. sunburn)<0.005.

TABLE 18
Effect of sunburn on hemoglobin content in rat skin and its reversal by trifluoperazine administered in the form of a cream

| Conditions | Hemoglobin (Absorption at 420 mµ) |
|---|---|
| Control | 0.16 ± 0.015 (18) |
| Sunburn | 0.50 ± 0.037 (7) |
| Trifluoperazine | 0.21 ± 0.019 (12) |

Values are means±S.E., with number of experiments in parentheses. P values (sunburn vs. control or trifluoperazine vs. sunburn)<0.005.

TABLE 19
Effect of sunburn on ATP concentration in rat skin and its reversal by trifluoperazine administered topically in the form of a cream

| Conditions | ATP (µmoles/kg wet wt.) |
|---|---|
| Control | 1135 ± 64 (10) |
| Sunburn | 476 ± 68 (5) |
| Trifluoperazine | 1297 ± 46 (9) |

Values are means±S.E., with number of experiments in parentheses. P values (sunburn vs. control or trifluoperazine vs. sunburn)<0.005.

TABLE 20
Effect of sunburn on the activity of soluble 6-phosphogluconate dehydrogenase in rat skin and its reversal by trifluoperazine administered topically in the form of a cream

| conditions | 6-phospogluconate dehydrogenase activity (m unit/mg protein) |
|---|---|
| Control | 20.70 ± 0.36 (8) |
| Sunburn | 13.77 ± 1.04 (5) |
| Trifluoperazine | 20.30 ± 0.97 (6) |

Values are means±S.E., with number of experiments in parentheses. P values (sunburn vs. control or trifluoperazine vs. sunburn)<0.005.

TABLE 21
Effect of sunburn on the activity of soluble and mitochondrial hexokinase in rat skin and its reversal by trifluoperazine administered topically in the form of a cream

| Conditions | Mitochondrial hexokinase activity (m unit/mg protein) | Soluble hexokinase activity (m unit/mg protein) |
|---|---|---|
| Control | 3.40 ± 0.17 (9) | 2.33 ± 0.09 (9) |
| Sunburn | 1.38 ± 0.08 (5) | 1.18 ± 0.09 (5) |
| Trifluoperazine | 2.19 ± 0.24 (9) | 2.46 ± 0.22 (9) |

Values are means±S.E., with number of experiments in parentheses. P values for soluble hexokinase (sunburn vs. control or trifluoperazine vs. sunburn)<0.005; for mitochondrial hexokinase (sunburn vs. control)<b 0.005; trifluoperazine vs. sunburn)<0.025.

The compound fluphenazine was used to determine its effectiveness in treating experimentally induced burns (100° C. water) on rat skin:

TABLE 22

| Conditions | Hemoglobin (Absorption at 420 mµ) |
|---|---|
| Control | 0.20 ± 0.02 (8) |
| Burn | 0.44 ± 0.05 (6) |
| Fluphenazine | 0.32 ± 0.03 (6) |

Values are means±S.E. with number of experiments in parantheses; P values: burn vs. control<0.005; fluphenazine vs. burn<0.005.

TABLE 23
Effect on burns of ATP concentration in rat skin and its reversal by fluphenazine

| Condition | ATP (µmoles/kg wet wt) |
|---|---|
| Control | 1017 ± 42 (6) |
| Burn | 391 ± 44 (6) |
| Fluphenazine | 680 ± 98 (6) |

Values are means±S.E. with number of experiments in parentheses. P values: burn vs. control<0.005; fluphenazine vs. burn<0.025.

TABLE 24

Effect of burns on the activity of Soluble 6-phosphogluconate dehydrogenase and its reversal by fluphenazine

| Condition | 6-Phosphogluconate dehydrogenase activity (m unit/mg protein) |
|---|---|
| Control | 18.37 ± 0.421 (6) |
| Burn | 6.92 ± 0.323 (6) |
| Fluphenazine | 9.69 ± 1.220 (6) |

Values are means±S.E. with number of experiments in parentheses. P values: burn vs. control<0.005; fluphenazine vs. burn<0.05.

TABLE 25

Effect of burns on the activity of soluble and mitochondrial hexokinase in rat skin and its reversal by fluphenazine

| conditions | Mitochondrial hexokinase activity (m unit/mg protein) | soluble hexokinase activity (m unit/mg protein) |
|---|---|---|
| Control | 2.85 ± 0.134 (6) | 2.09 ± 0.088 (6) |
| Burn | 0.78 ± 0.067 (6) | 0.67 ± 0.042 (6) |
| Fluphenazine | 1.48 ± 0.110 (6) | 1.07 ± 0.082 (6) |

Values are means±S.E., with number of experiments in parentheses. P values (burn vs. control or fluphenazine vs. burn)<0.005.

TABLE 26

Effect of burns on hemoglobin content in rat skin and its reversal by Haloperidol

| Conditions | Hemoglobin (absorption at 420 m$\mu$) |
|---|---|
| Control | 0.20 ± 0.01 (6) |
| Burn | 0.44 ± 0.02 (6) |
| Haloperidol | 0.26 ± 0.02 (6) |

Values are means±S.E., with number of experiments in parentheses. P values: burn vs. control<0.005; Haloperidol vs. burn<0.005.

TABLE 27

Effect of burns on ATP concentration in rat skin and its reversal by Haloperidol

| Conditions | ATP ($\mu$moles/kg wet wt.) |
|---|---|
| Control | 1151 ± 25 (6) |
| Burn | 322 ± 19 (6) |
| Haloperidol | 645 ± 49 (6) |

Values are means±S.E., with number of experiments in parentheses. P values: burn vs. control<0.005; Haloperidol vs. burn<0.005.

TABLE 28

Effect of pimozide on hemoglobin content in rat sunburned skin.

| Conditions | Hemoglobin (Absorption at 420 m$\mu$) |
|---|---|
| Control | 0.144 ± 0.015 (16) |
| Sunburn | 0.438 ± 0.043 (7) |
| Pimozide | 0.363 ± 0.034 (11) |

Values are means±S.E., with number of experiments in parentheses. P values: sunburn vs. control<0.005; pimozide vs. sunburn<0.05.

TABLE 29

Effect of pimozide on ATP concentration in rat sunburned skin.

| conditions | ATP ($\mu$moles/kg wet wt) |
|---|---|
| Control | 1231 ± 59 (10) |
| Sunburn | 360 ± 22 (7) |
| Pimozide | 428 ± 22 (11) |

Values are means±S.E., with number of experiments in parentheses. P values: sunburn vs. control<0.005; pimozide vs. sunburn <0.05.

TABLE 30

Effect of penfluridol on ATP concentration in rat burned skin.

| Conditions | ATP ($\mu$moles/kg wet wt.) |
|---|---|
| Control | 1127 ± 34 (6) |
| Burn | 346 ± 34 (6) |
| Penfluridol | 436 ± 33 (5) |

Values are means±S.E., with number of experiments in parentheses. P values: burn vs. control<0.005; penfluridol vs. burn<0.05.

TABLE 31

Effect of penfluridol on hemoglobin content in rat burned skin.

| Conditions | Hemoglobin (Absorption at 420 m$\mu$) |
|---|---|
| Control | 0.19 ± 0.02 (6) |
| Burn | 0.53 ± 0.04 (6) |
| Penfluridol | 0.42 ± 0.02 (5) |

Values are means±S.E., with number of experiments in parentheses. P value: burn vs. control<0.005; penfluridol vs. burn<0.05.

The following compositions may be utilized in the practice of the invention:

| TOPICAL OINTMENT | |
|---|---|
| trifluoperazine | 8.0 g |
| liquid petrolatum | 5.0 g |
| white petrolium | 87.0 g |
| | 100.0 g |
| TOPICAL CREAM | |
| trifluoperazine | 8.0 g |
| cetyl alcohol | 8.4 g |
| stearyl alcohol | 8.4 g |
| sodium lauryl sulfate | 1.4 g |
| white petrolatum | 27.6 g |
| propylene glycol | 9.2 g |
| water, to make | 100.0 g |
| TOPICAL LOTION | |
| a. trifluoperazine | 8.0 g |
| Oil of Olay | 92.0 g |
| | 100.0 g |
| b. trifluoperazine base* | 8.0 g |
| | 92.0 g |
| | 100.0 g |
| *stearic acid | 1.4 g |
| triethanolamine | 0.6 g |
| glyceryl monostearate | 4.0 g |
| lanolin, hydrous | 1.0 g |
| cetyl alcohol | 0.4 g |
| mineral oil | 2.0 g |
| methlparahydroxybenzoate | 0.1 g |
| distilled water | 90.5 g |
| perfume g.s. | |

| -continued | |
|---|---|
| | 100.0 g |
| SUNBURN PREVENTATIVE | |
| trifluoperazine | 8.0 g |
| para hydroxybenzoate | 3.0 g |
| base* | 92.0 g |
| | 100.0 g |
| *Topical lotion (b) | |
| SUNBURN TREATMENT | |
| trifluoperazine | 8.0 g |
| lidocaine | 2.0 g |
| base* | 92.0 g |
| | 100.0 g |
| *Topical lotion base (b) | |
| ANTINFECTION CREAM | |
| trifluoperazine | 8.0 g |
| bacitracin | 40,000 units |
| cetyl alcohol | 8.4 g |
| stearyl alcohol | 8.4 g |
| sodium lauryl sulfate | 1.4 g |
| white petrolatum | 27.6 g |
| propylene glycol | 9.2 g |
| water, to make | 100.0 g |
| ANESTHETIC/ANTINFECTION CREAM | |
| Trifluoperazine | 7.0 g |
| Bacitracin | 40,000 units |
| lidocaine | 1.0 g |
| cetyl alcohol | 8.4 g |
| stearyl alcohol | 8.4 g |
| sodium lauryl sulfate | 1.4 g |
| white petrolatum | 27.6 g |
| propylene glycol | 9.2 g |
| water to make | 100.0 g |
| SPRAY | |
| trifluoperazine | 8.0 g |
| propylene glycol | 92.0 g |
| INJECTABLE SOLUTION | |
| trifluoperazine | 2 mg |
| Ringer Lactate solvent | 1000 ml |
| FLASH BURN PREVENTIVE CREAM | |
| trifluoperazine | 8.0 g |
| bleached dewaxed shellac | 13.7 g |
| isopropyl alcohol, 99% | 28.48 g |
| linseed oil, Z-3 viscosity | 3.5 g |
| stearic acid, triple pressed | 0.15 g |
| triethylene glycol Di-2-ethylhexoate | 0.8 g |
| diethylene glycol monoethyl ether | 1.1 g |
| titanium dioxide | 37 g |
| sodium bicarbonate | 2.25 g |
| magnesium stearate | 8 g |
| menthyl salicylate | 2.5 g |
| wetting agent (sulfonated alcohol) | 0.3 g |
| iron oxide (lemon shade) | 1.6 g |
| mineral black | 0.62 g |

I claim:

1. A method for the treatment of burns, frostbite or sunburn to the skin, said method comprising administering to one who is afflicted with such burns, frostbite or sunburn, a compound having the ability to interfere with the action of calcium calmodium complex in an amount that is effective for the treatment of said burns, frostbite or sunburn.

2. A method for treatment of trauma to the skin defined in claim 1 wherein said trauma is induced by burns, sunburn or frostbite.

3. A method for the treatment of burns, sunburn or frostbite as defined in claim 2 wherein the compound is selected from the group consisting of phenothiazines, thioxanthenes, butyrophenones, diphenylbutylamines, dibenzodiazepines, benzodiazepines, dibenzazepines amd naphthalenesulfonamides that have the ability to interfere with the action of calcium calmodulin complex.

4. A method for the treatment of burns, sunburn or frostbite as defined in claim 3 wherein said compound is administered topically to the burned area.

5. A method for the treatment of burns, sunburn or frostbite as defined in claim 3 wherein said compound is administered parenterally.

6. A method for the treatment of burns, sunburn or frostbite as defined in claim 4 wherein said compound is applied as an ointment, cream, lotion or spray.

7. A method for treatment of burns, sunburn or frostbite as defined in claim 3 wherein said compound is applied in combination with a local anesthetic.

8. A method for the treatment of burns, sunburns or frostbite as defined in claim 4 wherein said compound is applied in combination with an anti-infective agent.

9. A method for the treatment of burns, sunburn or frostbite as defined in claim 4 wherein said compound is applied in combination with a local anesthetic.

10. A method for the treatment of burns, sunburn or frostbite as defined in claim 4 wherein said compound is applied in combination with a local anesthetic and an anti-infective agent.

11. A method for the treatment of burns, sunburn and frostbite as defined in claim 3 wherein the compound selected from trifluoperazine, fluphenazine, haloperidol, pimozide and penfluridol.

12. A method for the treatment of burns, sunburn and frostbite as defined in claim 11 wherein the compound is trifluoperazine.

13. A method for the treatment of burns, sunburns and frostbite as defined in claim 6 wherein the compound is trifluoperazine.

14. A method for the treatment of burns, sunburn and frostbite as defined in claim 7 wherein the compound trifluoperazine.

15. A method for the treatment of burns, sunburn and frostbite as defined in claim 8 wherein the compound is trifluoperazine.

16. A method for the treatment of burns, sunburn and frostbite as defined in claim 9 wherein the compound is trifluoperazine.

17. A method for the treatment of burns as defined in claim 5 wherein the compound is trifluoperazine.

18. A method for the treatment of burns, sunburn or frostbite as defined in claim 10 wherein the compound is trifluoperazine.

19. A method for the reduction of the burning effects of exposure of skin to the sun which comprises applying to the skin of a host who is to be exposed to sunlight, a compound that has the ability to interfere with the action of calcium calmodulin complex in an amount that is efffective to reduce the burning effect of exposure to the sun.

20. A method for the reduction of the burning effect of exposure of skin to the sun as defined in claim 19 wherein the compound is applied in combination with a sunscreening agent.

21. A method for the reduction of the burning effect of exposure of skin to the sun as defined in claim 20 wherein the compound is trifluoperazine.

22. A method for the reduction of damage to the skin due to frostbite, said method comprising treating to a host that is to be exposed to freezing conditions an amount of a compound, which is effective in reducing the damage to the skin due to frostbite.

23. A method for the reduction of damage to the skin due to frost bite as defined in claim 21, wherein the compound is trifluoperazine.

24. A method for the prophylactic treatment of trauma to the skin which comprises topically applying to one who is to be exposed to such trauma, a compound having the ability to interfere with the action of calcium calmodulin complex in an amount that is effective for the prevention of said trauma.

25. A method as defined in claim 24 wherein the compound is trifluperazine.

26. A composition for the therapeutic or prophylactioc treatment of trauma to the skin, said composition comprising an ointment, cream or lotion which contains from 4% to 40% by weight of a compound that has the ability to interfere with the action of calcium calmodulin complex and a topically effective anti-infective agent.

27. A composition for the therapeutic of prophylactic treatment of trauma to the skin as defined in claim 26 wherein the ointment cream or lotion contains from 7.5% to 20% by weight of the compound having the ability to interfere with the action of calcium calmodulin complex.

28. A composition as defined in claim 26 wherein said compound is selected from the group consisting of phenothiazine, thioxanthenes, butyrophenones, diphenylbutylamines, dibenzodiazepines, benzodiazepines, dibenzazepines and naphthalenesulfonamides that have the ability to interfere with the action of calcium calmodulin complex.

29. A composition as defined in claim 28 wherein the compound is trifluoperazine.

30. A composition for the treatment of trauma as defined in claim 22 which includes an effective amount of a local anesthetic.

31. A composition for the treatment of trauma to the skin as defined in claim 24 wherein the anti-infective agent is selected from the group consisting of neomycin, bacitracin, silver sulfadiazine, gentamicin, polymyxin and mafenide acetate.

32. A composition for the treatment of trauma to as defined in claim 31 wherein the compound having the ability to interfere with the action of calcium calmodulin complex is trifluoperazine.

33. A compound for the treatment of burns, sunburn or frostbite said composition comprising an effective amount of a local anesthetic and an amount of a compound having the ability to interfere with the action of calcium calmodulin complex in an ointment, cream or lotion.

34. A composition for the treatment of burns, sunburn or frostbite as defined in claim 33 wherein the compound is selected from the group consisting of phenothiazines, thioxanthenes, butyrophenones, diphenylbutylamines, dibenzodiazepines, benzodiazepines, dibenzazepines and naphthalenesulfonamides having the ability to interfere with the action of calcium calmodulin complex.

35. A composition for the treatment of burns, sunburn or frostbite as defined in claim 34 wherein the compound having the ability to interfere with the action of calcium calmodulin complex is trifluoperazine.

36. A bandage for aplication to skin trauma, said bandage comprising in combination an impervious backing layer and an absorbent layer containing a composition which comprises a compound having the ability to interfere with the action of calcium calmodulin complex.

37. A bandage as defined in claim 36 wherein the compound is trifluoperazine.

* * * * *